United States Patent [19]  
Harte et al.

[11] 4,340,564  
[45] Jul. 20, 1982

[54] IMMUNOADSORPTIVE SURFACE COATING FOR SOLID-PHASE IMMUNOSUBSTRATE AND SOLID-PHASE IMMUNOSUBSTRATE

[75] Inventors: Richard A. Harte, Redwood City; Max Bart, San Jose, both of Calif.

[73] Assignee: Daryl Laboratories, Inc., Santa Clara, Calif.

[21] Appl. No.: 170,632

[22] Filed: Jul. 21, 1980

[51] Int. Cl.³ .................... G01N 33/50; G01N 31/22
[52] U.S. Cl. ........................................ 422/56; 23/915; 422/57; 424/8; 424/12; 428/325; 428/326; 428/327; 435/5; 435/7; 435/805
[58] Field of Search ............... 422/57, 56; 435/7, 177, 435/180, 5, 805; 424/8, 12, 1, 1.5; 260/29.6 R; 428/327, 411, 326, 325, 331, 461, 462, 442, 441, 521, 463, 522, 532, 264, 274; 252/408 R, 318; 23/915

[56] References Cited

U.S. PATENT DOCUMENTS 3,770,383 11/1973 Price ..................................... 422/57
3,853,987 12/1974 Dreyer .................................... 424/1
3,950,600 4/1976 Knirsch et al. ..................... 428/327
3,992,517 11/1976 Lowke et al. .......................... 424/12
4,003,988 1/1977 Hoff et al. .............................. 424/12
4,042,335 8/1977 Clement ......................... 435/805 X
4,137,208 1/1979 Elliott ......................... 260/29.6 R X
4,241,143 12/1980 Ashie et al. ................ 260/29.6 R X
4,243,416 1/1981 Grourke et al. ........... 260/29.6 R X
4,258,001 3/1981 Pierce et al. ...................... 23/915 X

OTHER PUBLICATIONS

Rose et al., The Condensed Chemical Dictionary, 6th Ed.; Reinhold Publ. Corp., New York, 1961; pp. 438-439, 652-653.

Primary Examiner—Kenneth M. Schor  
Attorney, Agent, or Firm—Claude A. S. Hamrick

[57] ABSTRACT

A solid-phase immunosubstrate (14) which has a surface coating (12) composed of a water based emulsion of microdiameter sized latex polymer beads (16) and materials which act as light scattering centers (17), said surface coating (12) having an immunoreagent added thereto to form an immunoreactive immunosubstrate (27). An overcoating (28) being formed on said surface coating (12), said overcoating having a higher percentage of similarly sized latex polymer beads (16) contained therein.

2 Claims, 5 Drawing Figures

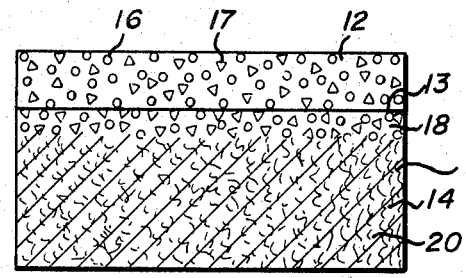
Fig_1
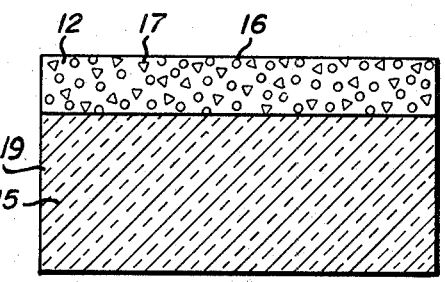
Fig_2
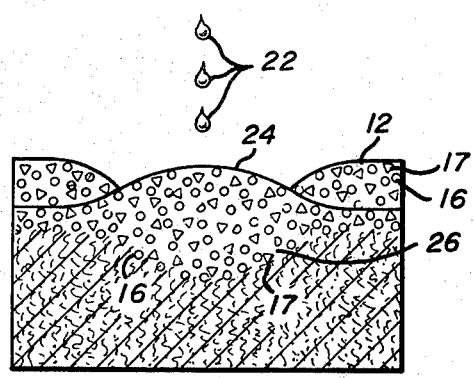
Fig_3
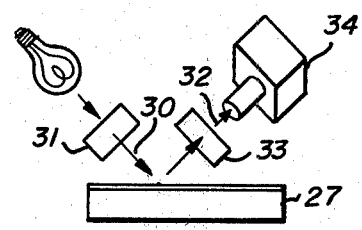
Fig_5
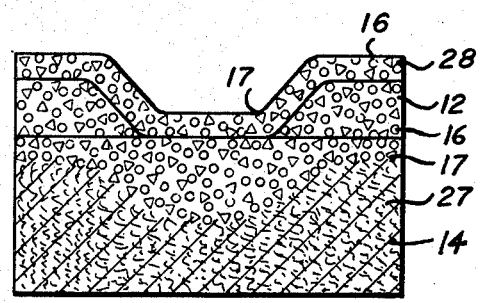
Fig_4

IMMUNOADSORPTIVE SURFACE COATING FOR SOLID-PHASE IMMUNOSUBSTRATE AND SOLID-PHASE IMMUNOSUBSTRATE

BACKGROUND OF THE INVENTION

1. Field of the Invention

The present invention relates generally to solid-phase immunosubstrates for use in immunological assaying and more particularly to a surface coating or film for application to a solid-phase surface and to the immunosubstrate formed by the utilization of the surface coating.

2. Description of the Prior Art

Many solid-phase surfaces are presently employed in immunological testing to which a protein, such as an antibody (specific immunoglobulin) or an antigen (any one of many protein or protein bound substances), may be adsorbed to form an immunosubstrate. The solid-phase may be a metallic surface, such as is employed in polarization change studies, or a glass or smooth plastic surface in which the protein is fixed onto the surface by air drying, heat denaturation or the use of organic fixing agents such as acetone, ethanol, methanol or formaldehyde. In some cases use is made of protein adherence to the polymer chains of certain plastics without a fixing process, such as in the adsorption of viral, bacterial, hormonal or other antigens to polypropylene and/or polystyrene test tube walls, beads or microtiter plates. Cellulose and cellulose derivatives, such as mixtures of cellulose acetates and cellulose nitrates, have also been utilized as adsorptive surfaces for protein binding.

These prior art solid-phase surfaces are generally utilized without any surface coatings to alter the adsorptive character of the surface. A common problem with such surfaces is that care must be taken when washing the surface during test procedures to prevent the immunoreagents or analytes that have adhered to the surface from being removed therefrom. Additionally, the use of an uncoated surface limits the user to the surface area of that surface for immunoreagent adsorption, whereas an immunoadsorptive coating on the surface has a thickness which creates an immunoreagent adsorptive volume, thus permitting the adsorption of a greater quantity of immunoreagent and increasing the sensitivity of the assay.

The surface coating or film of the present invention is applied to solid-phase surfaces to increase adsorption and retention of immunoreagents. Its main constituent is a water based emulsion of microdiameter size polymer beads to which may be added a material which imparts light scattering centers into the coating. No prior art is known to the inventors that utilizes such polymer beads within a surface coating for solid-phase surfaces, nor that combines them with a material providing optical properties that improves the fluorescent testing capability of the immunosubstrate formed through the use of the surface coating.

SUMMARY OF THE PRESENT INVENTION

It is therefore a primary objective of the present invention to provide a surface coating for a solid-phase surface which aids in the adsorbtion and retention of immunoreagents.

It is another object of the present invention to provide a surface coating which may be applied to both porous and non-porous solid-phase surfaces.

It is a further object of the present invention to provide a solid-phase immunosubstrate which is specifically useful in optical immunoassay techniques such as fluorescence studies or absorptometry or reflectometry with enzyme label utilization.

The immunoadsorptive surface coating of the present invention includes a water based emulsion of dispersed polymer beads of microdiameter size. Where the coating is to be used in an optical testing situation, such as fluorescence testing, additional materials may be added to the coating to provide light scattering centers within the coating. In the surface coating of the preferred embodiment, the polymer may be an acrylic, polyvinyl acetate or butadiene-styrene copolymer or a combination thereof, and a source of light scattering centers may be starch, titanium dioxide, silicon dioxide or finely powdered clay or a combination thereof. The coating is applied by standard coating techniques to a solid-phase surface to create the immunosubstrate of the present invention.

For particular applications of the immunosubstrate of the present invention, a droplet of a particular immunoreagent, such as an antibody or antigen, may be placed on the immunosubstrate to penetrate thereinto and bind therewith. The immunosubstrate, with the immunoreagent in place, is now ready for instantaneous future use for testing in the immunoassays associated with the particular immunoreagent. The immunoreagent may be added to the surface coating prior to the application thereof on a solid-phase surface to produce similar results.

As a further modification of the immunoreagent impregnated immunosubstrate of the present invention, humectants and flow enhancers may be added to the surface coating or as an additional overcoating to aid in the penetration of the immunosubstrate coating by a test serum.

A primary advantage of the surface coating of the present invention is that it is has greater adsorptive properties than non-coated solid-phase surfaces.

It is another advantage of the surface coating of the present invention that it will retain the adsorbed immunoreagent against vigorous washing.

It is a further advantage of the surface coating of the present invention that it contains light scattering centers which provide improved optical properties to the immunosubstrate.

It is an advantage of the coated immunosubstrate of the present invention that an immunoreagent may be placed thereon to impregnate the coating, whereupon the immunosubstrate contains the immunoreagent in a form ready for instantaneous future use.

These and other objects and advantages of the present invention will no doubt become apparent to those of ordinary skill in the art after having read the following detailed description of the preferred embodiments which are illustrated in the several figures of the drawing.

IN THE DRAWING

FIG. 1 depicts a magnified cross sectional view of the surface coating of the present invention as applied to a porous solid-phase surface;

FIG. 2 depicts a magnified cross sectional view of the surface coating of the present invention as applied to a non-porous solid-phase surface;

FIG. 3 depicts the addition of an immunoreagent to the immunosubstrate shown in FIG. 1;

FIG. 4 depicts the immunoreactive immunosubstrate shown in FIG. 3 after an over-coating has been applied thereto; and FIG. 5 depicts the utilization of the immunoreactive immunosubstrate of the instant invention in a fluorescent testing situation.

DETAILED DESCRIPTION OF THE PREFERRED EMBODIMENT

The surface coating for a solid-phase surface of the present invention comprises a water based emulsion of dispersed polymer beads of microdiameter size. The utilization of such polymer beads in a water based emulsion produces a superior substance for protein binding, and where the bound proteins are immunoreagents such as antibodies or antigens an excellent immunosubstrate is created. In the preferred embodiment, a bead diameter of 0.1 to 1.0 microns has been found to produce excellent results. Larger bead diameters present little problem until their size affects the consistancy of the coating or the ability of the beads to penetrate into a porous solid-phase surface as is hereinafter described. It is to be noted, however, that a larger bead size will also reduce the available bead surface area for protein binding. Almost any material having good protein binding properties and having the capability of being formulated into microdiameter size particles within a water based emulsion could be utilized in the instant surface coating invention. Materials producing superior results have proved to be in the general class of latex type polymers. Particular latex polymers such as acrylics, polyvinyl acetates and butadiene-styrene copolymers have provided excellent results in immunoreactions, and these polymers or combinations of them are utilized in the preferred embodiment. Many emulsifiers are known to those skilled in the art to create an emulsion of the water-bead mixture, a suitable emulsifier being an ammonium soap of a fatty acid.

Where the surface coating is to be used in an optical testing situation, such as fluorescent testing, the addition of a substance which specifically provides light scattering centers within the coating has proved to increase the fluorescence of the test sample created through use of the surface coating. Such scattering centers are important because it is the nature of the instant coating to permit immunoreagents to permeate therethrough, and the scattering centers within the coating aid in the optical detection of such permeating immunoreagents and their immunoreactions.

Suitable materials for providing light scattering centers have been found to be starch, titanium dioxide, silicon dioxide and finely powdered clays such as kaolin. However, the quantity of such materials must be controlled as an increase in non-specific binding of immunoreagents can be noted with increasing amounts of light scattering centers. This effect is particularly pronounced where titanium dioxide or clay is utilized.

The basic surface coating according to the present invention is therefore primarily a water based latex bead emulsion which may contain additional substances that contribute light scattering centers. Its basic formulation varies according to whether light scattering centers are to be added; thus its composition by weight may vary from approximately 30% latex polymer beads
69% water
1% emulsifying agent to a formulation including light scattering centers which has a composition by weight of approximately:

15% light scattering centers
15% latex polymer beads
1% emulsifying agent
69% water Further refinements of these basic formulations involve the addition of preservatives, surfactants, pH buffers, fungicides and defoamers to provide various properties to the surface coating that are helpful in the manufacture, storage and usage of the coating and immunosubstrate described hereinafter. Thus a formulation of a preferred embodiment of the surface coating of the present invention comprises the following approximate composition by weight:

4% butadiene-styrene copolymer
7% polyvinyl acetate polymer
4.5% titanium dioxide
6.8% silicon dioxide
0.5% preservation
0.1% pH buffer
0.5% fungicide
0.5% defoamer
4.0% surfactants
1.0% emulsifier
71.1% water The coating may be applied to a solid-phase surface by way of the standard application techniques; thus brushing, spraying, sponging, blade coating, rolling, dipping or droplet depositing, as well as other standard techniques, may be utilized for its application.

The coating may be applied to either porous or non-porous solid-phase surfaces. FIG. 1 is a cross sectional view of a surface coating 12 according to the instant invention as applied to a porous solid-phase surface 14 whereas FIG. 2 is a cross sectional view of a surface coating 12 according to the instant invention as applied to a non-porous solid-phase surface 15. The difference between the two coated surfaces of FIG. 1 and FIG. 2 is the penetration 18 of the coating 12 into the surface 13 of the porous solid-phase 14 which is not found where a non-porous solid-phase 15 is utilized. It is noted that the polymer beads 16 are shown as circular elements and light scattering particulates 17 are shown as triangular elements, both of which are shown disproportionately large to aid in understanding the invention. A porous surface 14 may consist of a paper-like material composed of matted cellulosic fibers 20. For use in optical analysis, such as by fluorescence, the fiber 20 diameters must be considerably larger than the wavelengths of visible light, such that any light entering the disordered matrix of fibers will be scattered about by reflections from the fiber-liquid interface. Fiber diameters exceeding 0.4 to 0.7 microns have been found to be quite suitable. Larger fiber diameters present little problem until their size affects the ability of the porous mesh to retain the coating in place. The light scattering centers component 17 of the coating is particularly important where the coating is applied to a porous surface, as good immunoassay results utilizing optical methods require light penetration to significant depths within the porous material. The light scattering centers aid in obtaining such light penetration.

A non-porous solid-phase surface 15 for the coating may be metal, glass or any of the various plastic materials that have been utilized in the prior art. The coating, when utilized on a non-porous surface, provides a thickness to the immunoadsorbant layer in which the immunochemical reactions occur. This thickness creates a volume in which reactions occur and, as it results in an increased amount of adsorbed immunoreagent per unit of surface area over a non-coated solid-phase surface, it thereby generally produces a more sensitive immunoassay than a non-coated solid-phase surface. A coating thickness of approximately 0.1 millimeters has been found to produce good results.

After a solid-phase surface has been coated, it is termed an immunosubstrate 19. As shown in FIG. 3, it may then be prepared for a particular immunochemical reaction by selecting an immunoreagent, such as a diluted antigen, antibody or enzyme solution, and wetting surface of the immunosubstrate with a few droplets 22 thereof. Humectants and wetting agents such as hydroxypropylmethyl cellulose may be added to the immunoreagent solution to speed the wetting process.

Where a porous surface has been utilized, the immunoreagent solution penetrates into the coating and wets the body of the porous material, causing fiber swelling 24. The polymer beads 16 and light scattering centers 17 are carred into the fibrous mesh of the porous material where they are entrapped 26. The immunoreagent is also carried into the mesh and adsorbed onto the entrapped polymer beads 16. The immunoreagent impregnated porous immunosubstrate is then allowed to dry. As the moisture evaporates during the drying process, the fibers return to their original unswollen size and positions, but now firmly enmesh the dried immunoreagent, thus providing an exceedingly stable immunoreactive immunosubstrate.

An alternative embodiment, that has been utilized for the production of an immunoreactive immunosubstrate, comprises the addition of an immunoreagent directly to the surface coating described hereinabove prior to the coating of a solid-phase surface. The addition of the immunoreagent to the surface coating creates an immunoreactive surface coating. Approximately 0.01% by weight of immunoreagent is added to the surface coating formulation in this embodiment. However, the amount of immunoreagent will vary depending upon the exact immunoreagent being utilized and the desired sensitivity of the immunoreactive immunosubstrate being formed. The immunoreactive surface coating may then be applied to a solid-phase surface in any of the above-mentioned standard application methods. The resulting immunoreactive immunosubstrate can be made everywhere reactive on its surface by a uniform coating of the immunoreactive surface coating on the solid-phase or it can be made reactive in localized areas by placing droplets of immunoreactive surface coating at discrete locations on the solid-phase.

As shown in FIG. 4, an immunoreactive immunosubstrate 27 may be made even more sensitive by then overcoating the surface thereof with a coating 28 of basically the same ingredients as the instant coating, but containing a higher percentage of the polymer beads 16.

A typical overcoating liquid comprises substantially the following formulation by weight:
Stock emulsion:
  10–20% light scattering centers
  10–25% latex polymer beads
  1% emulsifier plus water vehicle in amount to total 100% by weight of the stock emulsion.
To 100 ml of the stock emulsion is added:
  0.5 gm of carboxymethyl cellulose
  1 ml of polyvinyl alcohol
  1 ml of hydroxypropylmethyl cellulose as humectants and flow enhancers.

The immunoreactive immunosubstrate 27 may be utilized according to the following description. The immunosubstrate, having been previously impregnated with a specific antigen, is exposed to body fluid containing unknown amounts of an antibody directed at the specific antigen. The body fluid wets the coating and works its way through the thickness thereof. If the solid-phase is porous the body fluid penetrates into the mesh in the same manner as did the immunoreagent droplets 22. Any antibody present in the body fluid binds immunochemically to its specific antigen on the polymer beads.

After washing, to remove any fluid and unbound antibody, the immunosubstrate is exposed to an antihuman immunoglobulin made in another species (for example, goat antihuman immunoglobulin IgG or rabbit antihuman immunoglobulin IgM). If any of the human antibody had been present in the fluid it would be bound to the specific antigen within the coating, and the goat antibody would bind immunochemically to it as it worked its way through the coating thickness.

The goat antihuman antibody is labeled with a detectable tracer such as a radioactive tag, a fluorescent dye, or other standard tag. In the case of a radio label, such as iodine ($^{125}$I), a scintillation counter can be employed to quantitate the amount of label and, by calibration, the amount of human antibody bound in the immunological reaction.

Where a fluorochrome label such as fluorescein isothiocyanate (FITC) is utilized, any fluorometer capable of reading solid surfaces will be able to read the strength of fluorescence signal from the immunosubstrate, and thereby quantitate the amount of human antibody bound in the immunological reaction.

In one type of fluorescence testing, as depicted in FIG. 5, a blue photon 30 is isolated through the use of an excitation filter 31 and directed at the immunoreactive immunosubstrate 27. It will eventually either be absorbed by a molecule other than FITC, in which case it will raise the temperature of the immunosubstrate minutely by vibrational decay, or it will be absorbed by the FITC molecule, in which case, with a very high probability (greater than 90%), it will make a singlet-singlet transition and release one green photon. In its emersion from the FITC, however, the green photon will either be lost to absorption by some other molecules or it will come out 32 of the immunosubstrate for detection by a photoelectric transducer 34 through the use of an emission filter 33 which passes only green photons.

The advantage that occurs in an immunosubstrate containing many scattering centers, such as is described hereinabove, is that the bouncing about of the blue photon from the center increases its chance of eventual absorption by an FITC molecule which may not have been in its direct flight path. Also, the emerging green photon has a greater probability of being detected in a single direction if it makes many flight path changes, as are created by the scattering centers. Thus, the increase in number of scattering centers will tend to increase the fluorescence of the sample.

The instant surface coating and the immunosubstrates formed therefrom have been studied employing both radioactive and fluorescence labels and utilizing both antibodies and antigens as immunoreagents. The following examples will highlight their properties.

EXAMPLE I—Binding Capacity of the Immunosubstrate

Studies were carried out with radiolabeled (125$_I$) antibody (goat anti-human IgG) deposited in varying amounts on the surface of both a coated, porous surfaced immunosubstrate, as described hereinabove, and, as a control, on commercially available immunosubstrate films of mixed esters of cellulose which are used frequently for protein binding applications. A butadiene-styrene copolymer was utilized in the surface coating.

Both were subjected to counts in a gamma counter prior to and following four vigorous washing steps in buffers for 30 minute periods. From Table I it can be seen that at low protein loading (50 μgm) both surfaces bind comparably, losing about 30% in a first wash and about half by the end of the fourth wash.

As heavier protein loadings are employed, the immunosubstrate of the present invention shows considerably better binding properties. At 200 μgm of protein per unit of surface area, the mixed cellulose esters will lose almost 80% in the first wash, while the immunosubstrate will lose less than 50%.

TABLE I
RADIOACTIVE COUNTS (% Loss of Protein)

| CELLULOSE | Buffer | 50 μgm | 100 μgm | 200 μgm |
|---|---|---|---|---|
| Preassay | 174 | 320 | 502 | 966 |
| First Wash | 139 | 197 (38%) | 189 (62%) | 217 (78%) |
| Second Wash | 136 | 172 (46%) | 161 (68%) | 173 (82%) |
| Third Wash | 136 | 151 (53%) | 143 (72%) | 150 (89%) |
| Fourth Wash | 140 | 149 (53%) | 139 (72%) | 141 (85%) |
| IMMUNO-SURFACE | Buffer | 50 μgm | 100 μgm | 200 μgm |
| Preassay | 141 | 349 | 501 | 915 |
| First Wash | 143 | 254 (27%) | 282 (44%) | 488 (47%) |
| Second Wash | 143 | 242 (31%) | 282 (44%) | 412 (55%) |
| Third Wash | 140 | 189 (46%) | 256 (49%) | 359 (61%) |
| Fourth Wash | 136 | 185 (51%) | 256 (49%) | 334 (63%) |

EXAMPLE II—Mixed Antigens in the Substrate-Detection of a Mixture of Serum Antibodies For many years, rheumatologists and clinicians have relied on the ANA test (anti-nuclear antibodies) as a reliable screen for connective tissue diseases such as Systemic Lupus Erythamatosus (SLE) and Rheumatoid Arthritis (RA).

Since these diseases are characterized by the presence of several antibodies directed at different antigens within the nucleus of mammalian cells, all tests to date have employed whole cells as the substrate. These tests are generally performed with sliced tissue sections or cultivated cell lines in monolayers on glass microscope slides for subjective readout in a fluorescence microscope. One manufacturer has deposited whole suspended epithelial cells on a plastic substrate and read out the fluorescence objectively in a specially designed fluorometer.

The coating described hereinabove is capable of binding both cellular components and mixtures of solubilized antigens. ANA tests have thus been performed with cellular components consisting of salmon sperm nuclei separated from cells, and with a solubilized mixture of the most significant antigens considered stimuli to the anti-nuclear antibodies, such as double stranded deoxyribonucleic acid (D-DNA), nucleohistones (DNA-proteins) and ribonucleic acid (RNA).

This test is termed an ASNA (antibodies to soluble nuclear antigens) test.

Results reported with various antigen-substrate combinations are shown in Table II, including both porous and non-porous solid-phase immunosubstrates. A butadiene-styrene copolymer was utilized in the surface coating.

TABLE II
TESTS FOR ANA AND ASNA WITH VARIOUS IMMUNOSUBSTRATES

| Serum From Subject | Case Number | | | | |
|---|---|---|---|---|---|
| | #1 | #2 | #3 | #4 | #5 |
| #1. Healthy | neg | 33 | 56 | 55 | 57 |
| #2. Healthy | neg | 35 | 48 | 41 | — |
| #3. With connective tissue disease | — | 62 | 76 | 65 | 76 |
| #4. With Systemic Lupus | 4 + P/D | 101 | 102 | 100 | 102 |
| #5. With Systemic Lupus | 3 + D/S | 114 | 84 | 80 | — |

Case 1 - Standard microscope readout on rat liver slices. neg = no fluorescence, 3+ is bright fluorescence, P = peripheral staining, D = diffuse staining, S = speckled staining of the cell nucleus.
Case 2 - Suspended human epithelial cells fixed to solid plastic substrates and read in objective fluorometer. Fluorescence greater than 40 is positive for ANA.
Case 3 - Disclosed coating, blade coated on a porous cellulose base and wetted with the mix of soluble antigens (ASNA) or whole nuclei (salmon or herring sperm nuclei). Fluorescence greater than 60 is positive for ANA.
Case 4 - Liquid coating material, dropped onto solid plastic base, dried, then wetted with soluble antigens (ASNA). Fluoroscence greater than 60 is positive for ANA.
Case 5 - Soluble antigens (ASNA) blended into liquid coating material, then deposited on solid plastic base. Fluorescence greater than 60 is positive for ANA.

Comparison of the results for cases 3, 4, and 5 shows that the coating, as opposed to the surface to which it is applied, is a determining factor in the results obtained, and that the immunoreagent can be incorporated into the liquid surface coating prior to coating the solid-phase surface.

EXAMPLE III—Determining Antibodies to a Specific Viral Antigen in Body Fluid

Whereas Example II demonstrates that the instant coating is usable on non-porous as well as porous surfaces, in this Example a modification of the typical coating formulation is made. The amount of light scattering centers is reduced, and the polymer beads (emulsion of polyvinyl acetate beads) represents a much greater percentage of the coating. This coating is much like the overcoating stock emulsion formulation described hereinabove.

When this modified mixture is deposited in 25 μl droplets on a smooth, hard solid-phase surface, a thick coating is formed. While milky in its liquid state, it dries to clear, hard and glossy textured spots. To make this an immunoreactive immunosubstrate, 25 μl of commercially available rubella antigen is deposited on the film spots. The antigen, in aqueous suspension, penetrates the thick film spots and binds with the polymer beads therein. The immunoreactive immunosubstrate is allowed to dry for storage until it is to be used in an assay.

In an assay, upon incubation with diluted serum, plasma, urine, saliva, etc., the immunoreaction occurs in the wetted spot and a milkiness is manifested due to the difference in refractive index between the polymer beads and the aqueous medium. Since the test spot is read wet in a fluorometer, this milkiness provides much of the optical light scattering properties for which other materials such as starch, clay or titanium dioxide were previously employed.

In a study employing this immunoreactive immunosubstrate, a panel of 29 serum samples with known rubella hemagglutination (HAI) titer were tested employing immunofluorescence techniques. A simultaneous test was conducted with a mixed cellulose esters surface. The comparison of these two surfaces when related to HAI is seen in the data presented in Table III.

TABLE III
IMMUNOSUBSTRATE COMPARISON WITH HAI TITER

| HAI (29 samples) | CELLULOSE | IMMUNOREACTIVE IMMUNOSUBSTRATE |
| --- | --- | --- |
| Negative-11 | Negative-9 | Negative-11 |
|  | Positive-2 | Positive-0 |
|  | Specificity 82% | Specificity 100% |
| Positive-18 | Positive-15 | Positive-17 |
|  | Negative-3 | Negative-1 |
|  | Specificity 83% | Specificity 94% |
| Overall Agreement | Agree-24 | Agree-28 |
|  | Non-Agree-5 | Non-Agree-1 |
|  | Specificity 83% | Specificity 96.5% |

In comparing the data in Table III a significant reduction in the number of false positives and false negatives is shown. The immunoreactive immunosubstrate thus presents more reliable test results than the standard cellulose immunosubstrate.

It can therefore be seen that the immunoabsorptive surface coating of the present invention is a unique substance comprising a water based emulsion of polymer beads of microdiameter size to which light scattering centers may be added; the concentrations of these constituents being variable according to the above description. The coating has the ability to adsorb immunoreagents within its thickness whereby more sensitive testing is accomplished.

The coating may be applied both to porous and nonporous solid-phase surfaces to create an immunosubstrate which shows reduced loss of immunoreagent upon washing. Where an immunoreagent is added to the surface coating and allowed to dry on a solid-phase surface, an immunoreactive immunosubstrate is created having greater sensitivity and reliability than existing solid-phase surfaces.

Whereas, the preferred embodiments of the present invention has been described above, it is contemplated that other alterations and modifications may become apparent to those skilled in the art after having read the above disclosure. It is therefore intended that the appended claims be interpreted as covering all such alterations and modifications as fall within the true spirit and scope of the invention.

What is claimed is:

1. A solid-phase immunoreactive immunosubstrate for use in immunological assay determinations comprising:
a solid-phase surface;
a water based emulsion of dispersed latex polymer beads coating said surface and including latex polymer beads, water and an emulsifying agent to promote the emulsification of said beads within said water, said beads being of microdiameter size and composed of one of the substances from the group consisting of acrylic polymers, polyvinyl acetate polymers and butediene-styrene copolymers, and formed with a diameter of from 0.1 microns up to 1.0 microns, said coating further including a source of light scattering centers added to said coating to improve its fluorescent properties, whereby the concentration by weight of the components of said coating is approximately 15% light scattering centers, 15% polymer beads, 69% water and a 1% emulsifying agent;
an overcoating disposed over said coating and composed of a liquid emulsion having a composition by weight which includes 10-20% light scattering centers and 16-25% latex polymer beads of substantially identical size to those contained in said coating, plus a water vehicle in an amount sufficient to equal 100%, and having added to each 100 milliliters thereof, 0.5 grams of carboxymethyl cellulose, 1 milliliter of polyvinyl alcohol and 1 milliliter of hydroxypropylmethyl cellulose; and
an immunoreagent applied to at least one of said coating and said overcoating and adsorbed thereto to form an immunoreactive immunosubstrate for use in specific immunoreactions which require said immunoreagent.

2. A solid-phase immunoreactive immunosubstrate for use in immunological assay determinations comprising:
a solid-phase surface;
a water based emulsion of dispersed latex polymer beads coating said surface and including latex polymer beads, water and an emulsifying agent to promote the emulsification of said beads within said water, said beads being of microdiameter size and composed of one of the substances from the group consisting of acrylic polymers, polyvinyl acetate polymers and butediene-styrene copolymers, and formed with a diameter of from 0.1 microns up to 1.0 microns, said coating further including a source of light scattering centers added to said coating to improve its fluorescent properties;
said coating further including preservatives, surfactants, pH buffers, fungicides and defoamers, whereby the concentration by weight of the components of said coating is approximately 11% latex polymer beads, 11.3% light scattering centers, 0.5% preservatives, 0.1% pH buffers, 0.5% fungicides, 0.5% defoamers, 4.0% surfactants, 1.0% emulsifying agents, 0.01% immunoreagent and 71.09% water; and
an overcoating disposed over said coating and composed of a liquid emulsion having a composition by weight which includes 10-20% light scattering centers and 12-25% latex polymer beads of substantially identical size to those contained in said coating, plus a water vehicle in an amount sufficient to equal 100%, and having added to each 100 milliliters thereof, 0.5 grams of carboxymethyl cellulose, 1 milliliter of polyvinyl alcohol and 1 milliliter of hydroxypropylmethyl cellulose.

* * * * *